United States Patent
Balisky

(10) Patent No.: US 6,521,112 B1
(45) Date of Patent: Feb. 18, 2003

(54) PACED CHEMICAL REPLENISHMENT SYSTEM

(75) Inventor: Todd Alan Balisky, Riverside, CA (US)

(73) Assignee: Dj Parker Company, Inc., Santa Clara, CA (US)

( * ) Notice: Subject to any disclaimer, the term of this patent is extended or adjusted under 35 U.S.C. 154(b) by 0 days.

(21) Appl. No.: 09/743,729
(22) PCT Filed: Jul. 13, 1999
(86) PCT No.: PCT/US99/15752
§ 371 (c)(1), (2), (4) Date: Jan. 12, 2001
(87) PCT Pub. No.: WO00/03073
PCT Pub. Date: Jan. 20, 2001

(51) Int. Cl.[7] .............................................. C25D 21/18
(52) U.S. Cl. .................... 205/81; 118/689; 118/690; 205/82; 205/101; 422/105; 427/8; 436/55
(58) Field of Search ................ 205/98, 99, 101, 205/81, 82; 427/8; 118/689, 690; 422/105; 436/55

(56) References Cited

U.S. PATENT DOCUMENTS 5,182,131 A * 1/1993 Hashimoto et al. ............ 427/8
5,368,715 A * 11/1994 Hurley et al. .................. 205/82
5,484,626 A * 1/1996 Storjohann et al. ............ 427/8
5,631,845 A * 5/1997 Filev et al. .................. 364/510

* cited by examiner

Primary Examiner—Nam Nguyen
Assistant Examiner—William T. Leader
(74) Attorney, Agent, or Firm—Rohm & Monsanto

(57) ABSTRACT

A method of controlling the content of a chemical bath includes the steps of: determining a replenishment condition for the chemical bath; defining a unit of the replenishment condition; establishing a pacing factor corresponding to a replenishment volume of a replenishment medium per unit of the replenishment condition; and defining a replenishment threshold corresponding to the product of a predetermined number of the defined units of the replenishment condition and the pacing factor. The rate of continued replenishment of the predetermined constituent of the chemical bath is determined in response to the replenishment condition, which may be elapsed time, ampere-hours (or coulombs), number of product loads, product surface area, or line speed over time. The method replenishes constituents as they actually are consumed. It also prevents depletion (or buildup in the case of decanting a by-product) and the associated time delay related to detection and correction. The method is effective in controlling a copper electroplating operation.

14 Claims, 11 Drawing Sheets

FIG. 13

```
┌─────────────────────────────────────────────────────────────┐
│ ▭      Plater 1 Replenishment of Copper Sulfate          ▲▼ │
├─────────────────────────────────────────────────────────────┤
│                                                             │
│              Flow Sensor   [ Copper Sulfate    ▽]           │
│       ┌─ Settings ──────────────────────────────┐  [RESET]  │
│       │  ○    No Replenishment   Auto Add @ [29.000]│       │
│       │  ○    Printout           Target:      30   │        │
│       │  ◉    Automatic                            │        │
│       └────────────────────────────────────────────┘        │
│                                                             │
│       ┌─ REPLENISHMENT RATIO ──────────────────────┐        │
│       │  Add  [0.270]   liters per g/l below target│   130  │
│       │  Add  [0.0550]  liters per  [100]  amp-minutes│     │
│       │  Amp-minutes since last replenishment:  78  [Reset amp-min]│
│       └────────────────────────────────────────────┘        │
│                                                             │
│       ┌─ ADJUSTMENT ───────────────────────────────┐        │
│       │   No Adustment Required                    │        │
│       └────────────────────────────────────────────┘        │
│                                                             │
│       ┌─ MANUAL ADJUSTMENT ────────────────────────┐        │
│       │   [0.750]  liters requested        [Start] │        │
│       │   [0.750]  liters delivered        [Stop]  │        │
│       └────────────────────────────────────────────┘        │
│       [Edit Recipe]  [Tuning]            [Print]  [Close]   │
└─────────────────────────────────────────────────────────────┘
```

FIG. 14

| FEEDSTOCK | LEVEL | TOTAL | STATUS |
|---|---|---|---|
| Copper Sulfate | ▩ | 0.00 ltr | Ready |
| H$_2$SO$_4$ | ▩ | 0.00 ltr | Ready |
| HCl | ▩ | 0.00 ltr | Ready |
| MD | ▩ | 0.00 ltr | Ready |
| MLO | ▩ | 0.00 ltr | Ready |

140

▩ = okay    ▩ = low    ▩ = empty    ▩ = disabled    [Print]

FIG. 15

COPPER SULFATE SETTINGS

— FEEDSTOCK —
Total Delivered Volume:    0.000 liters            [Reset]
Low Level at:    [175.000]  liters
Delivery:    ○ Enabled    ○ Disabled    evel Status:  okay

150

— CALIBRATION —
Line:                            Tank:  [Tank #4 ▾]
Requested Volume:    [        ]
Liters Reported:    0.000 liters    ─── ◉ Total        [Start Delivery]
Liters Delivered:    [        ]         ○ Last         [Stop Delivery]
K Factor:    0.00                                     [Calibrate]

PACED CHEMICAL REPLENISHMENT SYSTEM

BACKGROUND OF THE INVENTION

1. Field of the Invention

This invention relates generally to systems for maintaining a predetermined concentration or balance of chemical constituents in a chemical bath, and more particularly, to a system that replenishes chemical components in accordance with historical replenishment rates that are modified in response to chemical analysis of the chemical bath.

2. Background of the Prior Art

Known arrangements and methods for maintaining a predetermined concentration or balance of chemical constituents in a chemical bath employ a control system that uses both, feed-forward (i.e., predictive) and feed-backward control. The feed-backward control relies on sensor inputs relating to constituent concentrations, plating efficiency, current output from the rectifier, drag-out rate, plating solution volume/liquid level, temperature and plating thickness.

The feed-forward control relies on a predictive model. In the context of an electroplating process, the changes in composition of the plating bath due to anode and cathode reactions are quantitatively modeled as a function of current-time. Additionally, the changes through drag-out are also modeled as a function of current-time. These are combined to obtain an overall system model. Oftentimes, materials or mass balance equations are applied to the model to calculate replenishment as a function of current-time to compensate for the losses and to maintain constant bath composition.

Known arrangements employ a microprocessor to compare the sensor signals obtained by the feed-backward control sensors against set points obtained by the predictive model and control/tolerance limits. If the values exceed the control/tolerance limits, the system can (1) recommend additional replenisher additions; (2) recommend postponing upcoming fee-forward additions for a determined period of ampere-time; and/or (3) assist the user in bringing the bath parameters back into their desired ranges via diagnostic screens.

The known systems are complicated and not very accurate. There is a need for a system that is effective at adjusting an historical trend in replenishment additions, and which does not rely on adjustment of a predictive model to effect the replenishment.

SUMMARY OF THE INVENTION

The present invention, in a first aspect thereof, is in the form of a method of controlling the content of a chemical bath. This method aspect of the invention includes the steps of:

first determining a rate of continued replenishment of a predetermined constituent of the chemical bath;

second determining a replenishment condition for the chemical bath; and adjusting the rate of continued replenishment of the predetermined constituent of the chemical bath in response to the replenishment condition.

The rate of continued replenishment in the step of first determining is based on an historical replenishment rate. The step of second determining a replenishment condition includes, in one embodiment of the invention, the step of monitoring elapsed time. In other embodiments, the step of second determining a replenishment condition includes, for example:

monitoring the consumption of electrical energy by the chemical bath;

monitoring the number of products to be plated in the plating bath; and/or monitoring the surface area of the products to be plated in the plating bath.

In a further embodiment of the invention, the step of first determining a rate of continued replenishment includes the steps of:

first establishing a quantum of a replenishment medium; and third determining a replenishment frequency corresponding to a rate at which the established quantum of a replenishment medium is deposited in the chemical bath with respect to the replenishment condition. This embodiment may further include the further steps of:

defining units of the replenishment condition; and counting elapsed units of the replenishment condition.

In this embodiment, there is further provided the step of defining a replenishment threshold corresponding to the product of the defined units of the replenishment condition and a predetermined number of units of the replenishment condition. The step of adjusting the rate of continued replenishment includes the step of comparing a counted number of units of the replenishment condition to the predetermined number of units of the replenishment condition. Additionally, the step of adjusting the rate of continued replenishment includes the step of determining a rate of adjustment of the rate of continued replenishment.

In accordance with a further method aspect of the invention, there is provided a method of controlling the content of a chemical bath, the method comprising the steps of:

determining a replenishment condition for the chemical bath;

defining a unit of the replenishment condition;

establishing a pacing factor corresponding to a replenishment volume of a replenishment medium per unit of the replenishment condition; and defining a replenishment threshold corresponding to the product of a predetermined number of the defined units of the replenishment condition and the pacing factor.

In one embodiment of this further aspect of the invention, there is provided the further step of counting elapsed units of the replenishment condition. Other embodiments include the steps of effecting a replenishment of the chemical bath when the replenishment threshold is reached, testing the chemical bath to determine the content of the chemical bath, and adjusting the quantum of the replenishment of the chemical bath in the step of effecting a replenishment of the chemical bath. The step of adjusting the quantum of the replenishment of the chemical bath is effected in accordance with the relationship:

$$P_F' = P_F \times [1 + (RA/T) \times A]$$

which is described in greater detail hereinbelow. This embodiment may include the step of adjusting the replenishment of the chemical bath and includes the further step of varying the replenishment threshold. In still further embodiments of the invention, the step of adjusting the quantum of the replenishment of the chemical bath includes the further step of varying the replenishment volume of the replenishment medium per unit of the replenishment condition.

Replenishment

The replenisher aspect of the present invention is a combination of software, computer/controller hardware, and chemical dispensing hardware that is able simultaneously to:

Receive commands and send responses or status to a host computer.

Receive commands and send responses or status to a user keypad and display terminal.

Start, monitor, and stop multiple chemical deliveries independently to multiple destinations.

Some of the parameters monitored or tracked by the system are:

Chemical flow rate

Chemical usage, cumulative

Chemical supply status (OK, low, empty)

Pump status (on, off, disabled)

Pump calibration factors

The following are employed to achieve accurate, variable and verified delivery volumes:

flow rate is limited to an approximate, predetermined value;

flow volume is measured by summing pulses from a paddle wheel flow sensor in the flow path;

flow is stopped when the intended volume is delivered by means of a shutoff valve.

The advantages of this approach are: 1) By limiting flow rate, the flow sensor is kept in a linear and, more importantly, reproducible volume per pulse range, thereby ensuring a high degree of accuracy. 2) By summing pulses and stopping at the desired pulse count (or volume), a variable, predetermined amount may be delivered, this system being considerably simpler than a variable flow rate system. 3) By using a flow sensor in place of, for example, a volumetric metering pump, the volume delivered can be verified rather than assumed.

The foregoing, in combination with the flow rate limiting method shown below (FIGS. 16 and 17), is less costly than other mechanical methods to deliver a variable volume. The use of a pneumatic pump with a constant pressure air supply provides feedstock at a constant pressure to a restricting needle valve or orifice. This method achieves the advantages of low cost and mechanical simplicity. The method attains its best accuracy, an important feature of this method, when the pump is used at approximately 1% to 10% of its flow rate capacity. Chemical flow rates are monitored during delivery. Very low or stopped flow rates are used to detect and to provide alarm indications of empty chemical supply conditions. This is used in place of an "empty" supply level detector, which may or may not indicate what actually is available to a pump. Moreover, the flow rate, the accumulated amount delivered since start of delivery, and the total amount delivered since reset or refill of feedstock, are reported during delivery.

Paced Replenishment

The paced replenishment system of the present invention refers to replenishment at a rate that is proportional to some event, hereinafter referred to as the replenishment condition. Suitable events that constitute the replenishment condition include elapsed time, ampere-hours (or coulombs), number of product loads, product surface area, line speed over time, etc. The method of the present invention replenishes process constituents as they actually are consumed. It also prevents depletion (or buildup in the case of decanting a by-product) and the associated time delay related to detection and correction.

As previously noted, precision replenishment is a critical aspect of the inventive system. In respective embodiments, replenishment is automatically initiated at the following replenishment conditions:

Based on analysis result

Based on amp-minutes

Based on production

Based on Process time

Based on elapsed time

Based on operator request

In one embodiment, the system permits the operator to set the replenishment delivery calculations, based on analysis result and amp-minute accumulation (or other replenishment condition listed above) for each parameter/chemical(s). Once these settings are established, the system will automatically adjust the replenishment amount based on amp-minutes by the analysis result(s) for that plating bath.

For this replenishment tuning feature to be functional, a communications link is provided between the plating tool and the controller of the inventive system. This link will inform the system of amp-minutes(amperage), by plating cell/bath, so that it can initiate replenishment based on, for example, an amp-minute target.

More specifically, replenishment of a chemical bath proceeds at a predetermined rate that may be based on historical experience with the particular operating bath. Alternatively, the existing replenishment rate in effect in a given system may be predetermined based on experience with similar or related chemical systems. In accordance with an embodiment of the invention, the rate of replenishment is carried out in small batches, or aliquots, of a user-defined volume at a frequency controlled by the time required for the pacing signal to reach the trip point. The trip point is a predetermined sum of paced unit(s), for example, 10.0 ampere-minutes or 3 product loads. The volume delivered after the trip point is reached is defined by the following relationship, which corresponds to the volume delivered on or after the real time paced units accumulate to equal or excess this paced units trip point:

$$\text{Replenishment volume} = P_F \times P$$

Where, $P_F$=Pacing factor, in units of replenishment volume per paced unit accumulated P=Paced units accumulated of the replenishment condition The paced units are continuously accumulated in real time. Also, the chemical bath is sampled periodically to determine whether the rate of replenishment is adequate to maintain the desired balance of chemical constituents. In situations where the result of the sampling indicates that the chemical bath is under-concentrated, as would be the case where too much $H_2O$ is added or decanted, or replenishment is delayed or inadequate, the volume of the next single delivery of the replenishment material is increased. Alternatively, the replenishment volume is maintained the same, but the subsequent replenishment is caused to occur sooner, essentially by retaining unused but accumulated paced units.

In a further embodiment of the invention, the replenishment ratio, i.e., the pacing factor, is adjusted in response to intermittent quantitative analyses. That is, the ratio of feedstock is replenished in proportion to the accumulated signal or pacing factor. Since the equipment of the present invention can perform accurate intermittent quantitative analyses on the content of the chemical bath, the results of such analyses are used intermittently to adjust the ratio of replenishment to accumulated pacing factor. In embodiments where the invention is employed for metal finishing chemical baths, the time interval for ratio adjustment, or tuning, ranges from one half hour to several hours, depending on the extent to which the process is dynamic, and its predictability.

Tuning is performed, in a highly advantageous embodiment of the invention, immediately after each analysis result is obtained. The adjustment, or tuning, is effected in accordance with the following equation:

$$P_F' = P_F \times [1 + (R_A/T) \times A]$$

Where, $P_F$=Current pacing factor, in units of replenishment volume per paced unit $P_F'$=New pacing factor R=Replenishment amount calculated from current quantitative analysis result. This calculation is usually stoichiometric.

T=Total paced replenishment since last analysis result. This excludes any amounts replenished for other reasons, such as in response to an analysis or operator request.

A=Fractional adjustment rate, $0 < A \leq 1$. A controls how fast the pacing factor is tuned. Processes which require a quick response and have high analytical certainty use a setting of A near 1.0. Processes which are less dynamic or have lower analytical certainty use a lower setting for A, such as less than 0.5.

In comparison to standard PID (Proportion, Integral, Derivative) control, the method of the present invention recovers from integral error (a constant offset) by replenishing the total amount necessary to return to the process control set point after each analysis. Integral error is intentionally not taken care of by the ongoing paced replenishment alone, is to avoid subsequent overshoot and correction after the set point is reached and to accomplish more immediate recovery.

Overshoot is corrected by pausing paced replenishment until a volume of delivery is bypassed (not delivered) equaling the calculated volume that would have caused the overshoot. The tuning equation is used as always, expect that the R term becomes negative. As is the case with integral error, this avoids subsequent undershoot and correction alter the set point is reached and to accomplishes a more immediate recovery.

In a specific illustrative embodiment of the invention, the implementation of the invention includes:

1. pacing signal conditioning to convert or amplify the signal to an acceptable range;
2. signal conversion to digital form;
3. signal integration, to produce a sum of the input over time;
4. comparison of the integrated signal against a trip point at which a small dose of replenishment is initiated; and
5. delivery of a present replenishment amount and reset of the signal integral to zero.

Chemical Concentration Control (Further Embodiment)

Tuning

Tuning, in accordance with a further embodiment of the invention, is based on the following:

When an analysis result is obtained, the change in analytical reading since the last analysis is calculated. If result averaging is in effect, this same equation applies but the Current Reading is replaced with the average of the current and previous n readings and the Previous Reading is replaced with the average of the previous reading and its corresponding previous n readings.

Change in Analytical Reading=Current Reading−Previous Reading

Then, the extent to which replenishment lacked (−) or was over-delivered (+) to have no change in reading is calculated. The contribution of other, non-paced replenishments is also accounted for in the equation:

Paced Replenishment Error=Change in Analytical Reading×Analytical Replenishment Factor−Sum of Non-Paced Replenishments Since Last Analysis where, "Analytical Replenishment Factor" is the multiplier used to convert an analytical result to a replenishment quantity. It is expressed in replenishment units over analytical units, such as liters replenishment per gram/liter below target. The "Sum of Non-Paced Replenishments Since Last Analysis" includes all replenishments that are not time or amp-minute based, such as the one in response to the previous analysis result or those done manually. A new replenishment factor is then calculated in accordance with the formula:

New Factor=Old Factor−Old Factor×(Tuning Rate/100)×Paced Replenishment Error/Sum of Paced Replenishments Since Last Analysis where, "Tuning Rate" is the rate of tuning, expressed as a percentage from 0 to 100.0. A typical operating value is 20.0. It depends on the analysis error, analysis frequency, and rate of process change. That is, the user will set it in proportion to (rate of change/analysis error/analysis frequency).

Another equation, derived for a two factor tuning method, affords the advantage of not "getting stuck" if the factor reaches zero. It is first a calculation for "Ideal Factor," which is the factor if all readings and data are perfectly accurate.

Total Chemical Consumed=−Change in Analytical Reading×Analytical Replenishment Factor+Sum of All Replenishments Since Last Analysis Ideal Factor=Total Chemical Consumed Pacing Units Accumulated Since Last Analysis or Ideal Factor=(−Change in Analytical Reading×Analytical Replenishment Factor+Sum of All Replenishments Since Last Analysis)/Pacing Units Accumulated Since Last Analysis and New Factor=Old Factor×(1−Tuning Rate/100)+Ideal Factor×(Tuning Rate/100)

Note that with these equations tuning is skipped if the "Pacing Units Accumulated Since Last Analysis" is zero.

Two Factor Tuning

When two different factors such as amp-minutes and time deplete the solution are to be considered, the factors must be determined algebraically since they usually deplete simultaneously but at different rates. The equations are most easily solved without the "Tuning Rate" terms. These are subsequently added.

Paced Replenishment Error 1=Change in Analytical Reading Due to 1×Analytical Replenishment Factor−Sum of All Replenishments Since Last Analysis+Sum of Paced Replenishments 1

Change in Analytical Reading Due to 1=Paced Units 1×Ideal Pacing Factor 1 where, "Paced Units 1" is the sum of the paced units that were reported since the last analysis, such as amp-minutes. And where "Ideal Pacing Factor 1" is the actual, but unknown, conversion factor to convert from paced units to replenishment amount. This gives:

Paced Replenishment Error 1=Paced Units 1×Ideal Pacing Factor 1×Analytical Replenishment Factor−Sum of All Replenishments Since Last Analysis+Sum of Paced Replenishments 1

Paced Replenishment Error 2=Paced Units 2×Ideal Pacing Factor 2×Analytical Replenishment Factor−Sum of All Replenishments Since Last Analysis+Sum of Paced Replenishments 2

Total Paced Replenishment Error=Change in Analytical Reading× Analytical Replenishment Factor−Sum of All Replenishments Since Last Analysis+Sum of Paced Replenishments 1+Sum of Paced Replenishments 2 or:

Total Paced Replenishment Error=Paced Replenishment Error 1+Paced Replenishment Error 2

To shorten the equations:

$A$=Total Paced Replenishment Error $B$=Analytical Replenishment Factor $E1$=Paced Units 1

$E2$=Paced Units 2

$X1$=Ideal Pacing Factor 1

$X2$=Ideal Pacing Factor 2

$C$=Sum of All Replenishments Since Last Analysis $D1$=Sum of Paced Replenishments 1

$D2$=Sum of Paced Replenishments 2

$F$=Change in Analytical Reading $O$=Analytical Replenishment Factor

Paced Replenishment Error $1=E1\times X1-C+D1$

Paced Replenishment Error $2=E2\times X2-C+D2$

Total Paced Replenishment Error$=F\times G-C+D1+D2$

Since:

Total Paced Replenishment Error=Paced Replenishment Error 1+Paced Replenishment Error 2 then substituting gives:

$$F\times G-C+D1+D2=E1\times X1-C+D1+E2\times X2-C+D2$$

Rearranging for X1 gives:

$$X1=(F\times G-C+D1+D2+C-D1-E2\times X2+C-D2)/E1$$

Combining terms gives:

$$X=(F\times G+C-E2\times X2)/E1$$

or:

Ideal Pacing Factor 1=(Change in Analytical Reading×Analytical Replenishment Factor+Sum of All Replenishments Since Last Analysis−Paced Units 2×Ideal Pacing Factor 2)/Pacing Units 1 and

Ideal Pacing Factor 2=(Change in Analytical Reading×Analytical Replenishment Factor+Sum of All Replenishments Since Last Analysis−Paced Units 1×Ideal Pacing Factor 1)/Pacing Units 2

Since these are two equations with two unknowns, they must be solved using two sets of data, namely, using the current to previous pair as one set and the previous to previous-previous pair as another set. Matrix algebra should suffice for this. The above equation can be simplified if constant terms are combined:

$$X=K/E1-X2\times E2/E1$$

and $$X2=K/E2-X1\times E1/E2$$

where, $$K=F\times G+C$$

Visual Basic User Interface

The Visual Basic User Interface (the Manager program) should include the following features:

1. A text box for entering the rate of tuning for each factor. This is a percentage, expressed from 0 to 100.0. The default for this is 100.0, which should be set lower only if the rate of consumption in proportion to the pacing factor is inconsistent.
2. A check box for selecting whether to hold off paced replenishment so that the concentration can return to target if it is high. The default for this box is true.
3. A text box for entering the number of previous readings (0 to 10) to use in calculating corrective replenishment or hold off volume. The default value is two, which is set higher when needed to smooth out more analytical error. The text box caption should be, for example, "Use average of current and previous results."

Level Control

Level control in chemical process solutions is challenging because of the variety of conditions that are encountered. There are consequently many methods of level sensing, each with its own strengths and vulnerabilities. Surface foam, for example does not present a problem to most radio frequency (RF) level sensors, but registers as liquid to an ultrasonic or acoustic-sensor. RF sensors, however, are inoperative when lightly coated or when in low conductivity solutions.

Durability (or reliability) is also a problem. The electronics associated with most sensors inherently have a limited temperature operating range beyond which the sensor can be destroyed. Another example is that maintenance becomes problematical when a solution coats or crystallizes on surfaces. Finally, space constraints often limit where a sensor can be installed. Usually, it is the sensor head (or electronics package) that causes these space problems. For example, above an open tank it is common for a hoist to be used to move material being processed in and out of the tank. This "material flow" limits what space is available for locating equipment above the tank liquid surface.

The present system employs a pneumatic level sensing technique in order to solve or prevent the aforementioned problems. (See, FIGS. 16 and 17) In general, this technique uses 1) a pressure regulated air or gas source, 2) a precision orifice or needle valve to limit the gas flow rate, 3) a pressure switch or sensor to detect the pressure within the tube and 4) a length of tubing of material inert to the process solution which is immersed in the solution and which internally takes on the pressure of the liquid at the depth where it terminates.

The orifice restricts airflow such that the pressure to the right (downstream) of the orifice is limited to the pressure head of the liquid above the bubbling tube outlet. A change in level is detected by the change in gas pressure required to keep the gas and liquid in equilibrium at the tube outlet. After the level rises, the gas will build in pressure until it equals the liquid pressure at the outlet, after which it will vent (bubble) and remain at equilibrium.

In some embodiments of the invention, there are employed:
1. a low pressure gas, for example less than 2 psi, to supply the system. This limits the maximum possible pressure and thus prevents damage to the low range pressure switch or sensor should the tube outlet become blocked;
2. a fine orifice, for example 0.008 to 0.020 inch diameter. This slows gas flow, allowing it to assume a pressure equal to the immersed liquid head height. It also is sufficient to keep the inside of the tube free of chemical coating and thus prevent buildup. This is particularly beneficial in solutions which otherwise dry and cake at air-liquid junctions. Although the invention is not limited to these orifice sizes, these sizes we have chosen have worked well in a practicable embodiment.
3. oversized tubing. By using tubing much larger than required, for example ⅜ inch diameter instead of ⅛ a inch, all measurable pressure drop attributable to air flow is eliminated. This allows the pressure sensor and associated equipment to be placed remotely from the solution in a safe, convenient and/or centralized location. In a practical embodiment of the invention, up to one hundred feet of distance has been used with no loss in performance.
4. a tube or pipe section in contact with the solution can be further oversized, for example to ½ inch or even 1 inch diameter, so that plugging of the outlet such as by dried material is much less likely. While plugging of the outlet has not been a problem in the practical embodiment, this technique may be useful in certain solutions.
5. Where inert, higher cost material is required in contact with the solution, a connection may be provided to convert from one tubing of standard material, such as nylon, polyurethane, or polyethylene to an inert material, such as Teflon®, prior to entering the solution. This also has the advantage of providing a convenient way to replace the immersed tube or pipe section should it become damaged or fouled.
6. By using two level sensors immersed at a fixed, known vertical distance apart, the pressure readings may be corrected for changes in solution density before converting the reading to level or volume. Of course, this method only applies to continuous analog level sensing, not discrete point level switching. The software used in conjunction with this level measurement method accomplishes the following:
1. "Debouncing" of the wave action in the tank. Since the tank solutions being measured undergo agitation, either intentionally or by work flow, the level is not constant, but is actually wavy. The software removes this "noise" switch type level detection to give a consistent, useful reading. The method for doing this, however, is not just to create a large hysteresis (or deadband) in the switch, and thus lessen precision, but is to sum and average "high" and "low" (on and off) readings. Thus if over a five second period a total of eight high and two low readings are obtained, the level is calculated to be at the 80% of the switching range. This integer value is used to attain precise control within a narrow range. The programmer, for example, may set the refill to begin at 70% and end 80%.
2. A further improvement on this technique has been to use a weighted average where the most current readings have the most weight. The simplified equation for this is:

New average level=(((100−W)×Previous average level)+(W×Current level reading ))/100, where the Current level reading is either zero or one and "W" is the weight to give to the newest reading. A typical range for "W" is 5 to 20, depending on how quickly a change in tank level is to be responded to (higher "W") versus how much dampening of wave action is desired (lower "W"). This weighting technique is applicable to both discrete and analog sensors.
3. With this approach, wave action can be used to confirm the functionality of target level sensor. Any reading between (but not including) 0% to 100% confirms that the switch is responding to level changes, such as caused by wave action. By starting filling when level is in the switching range—a normal mode of operation—slight agitation in the tank can be used to confirm sensor functionality.
4. A user settable control also allows automatic overfill, if desired, so as to reduce switch and fill valve cycling and thus increase in mechanical component life span.
5. Where two level sensors are used, each one is also used to confirm the proper operation of the other. When installed at different levels, the lower sensor is used as the process or target level; the higher sensor is used as an alert or warning level. When arranged in this way, if the lower sensor reads anything less than 100%, the only valid reading for the higher sensor is 0%. It is only when the lower sensor reads 100% that the higher sensor may read more than this. Conditions outside of this are reported as errors to the operator and are interlocked in the software to prevent hazardous or overfill operations. (It is common in the industry to use two sensors where the signal from one is used to turn on a filling or emptying device and from the other to turn it off. Thus the second sensor cannot be used to back up the first because it must be employed in the level control operation. For protection or interlocks a third sensor is required.
6. As a further protection against failure, software timers are employed to stop filling and alert the operator if the level does not 1) measurably rise within a preset time or 2) reach target within a (longer) preset time. Automated filling is not allowed until after an operator initiated reset occurs or the level is restored to the target by some external means.
7. This creates a failsafe design, which means that failure of the sensor(s) does not create a further hazard. A false high sensor reading results in no filling action; a false low results in a timed out filling attempt. (The filling time limit is set equal to less than the time required to fill the tank from the sensor to the rim.)

Specific Copper Plating Embodiment

In a specific illustrative embodiment of the invention that is adapted specifically for a copper plating environment, the system is designed to eliminate the need for manual analysis and replenishment of the chemicals associated with the control parameters of the copper plating baths. The system of the present invention also provides automatic sensor calibration and internal system diagnostics maintain a high degree of reliability, repeatability, and throughput performance. In addition, efficient trouble shooting and reduced maintenance requirements are achieved.

In this embodiment, an automatic analyzer is provided for copper sulfate, sulfuric acid, hydrochloric acid and two organic agents/additives. In a highly advantageous embodiment, the analyzer automates titrametric procedures and delivers sharp, distinct end-points in approximately five to seven minutes. With time spent for sampling, purging, sample preparation, redundant analysis, cleanup and trend checking, is included, the overall cycle time is therefore approximately between twenty and thirty minutes.

More specifically, this embodiment of the invention achieves automatic,

| chemical analysis of: | and chemical replenishment of: |
|---|---|
| copper | copper sulfate |
| sulfuric acid | sulfuric acid |
| chloride | hydrochloric acid |
| additive #1 | organic agent |
| additive #2 | organic agent |

The analyzer of the present invention will also automate cyclic voltammetric stripping for the analysis of the organic components, as well as provide indication of the total organic contamination of the plating solution. These analyses, when selected to be performed for a particular tank, are programmed to run concurrently with the analysis for the inorganic components. Within the method (titration or CVS or CPVS), analysis will occur in sequence.

Housing

The system of the present invention is, in a highly advantageous embodiment, housed in a fire retardant polypropylene cabinet with see-through front, hinged (locked) door. The system uses a pH electrode, an ORP electrode, a chloride-ion-specific electrode, and a cyclic voltammetric stripping unit to automate the necessary analytical procedures. This cabinet is equipped with leak detection and secondary containment and is designed to accept chemical samples from up to three (3) pressurized sample lines.

The cabinet also houses a manager system that is provided with a viewing screen for monitoring various forms of activity, a CPU shelf, a pull-out keyboard locking drawer, printer stand and electrical panel for a local control unit (LCU). The overall approximate size of this cabinet, in a practical embodiment, is 48"W×72"H×24"D. The analyzer is connected to the manager, in this embodiment, via a RS422 data transfer arrangement. The LCU is a combination of software, computer or controller hardware, signal conditioning modules, sensors and actuators. It is used to monitor, control and report a variety of physical parameters including temperature, level, conductivity, pH, voltage, current, pressure, flow, and other parameters that can be measured by a sensor. It is employed where continuous monitoring and/or immediate control response is required. Also, it condenses continuous sensor readings into maximum, average, and minimum values over specified time periods and reports them to a supervisory computer (or Manager) as such. This approach both improves local monitoring and control response and reduces the computing and communications burden on the supervisory computer.

Chemical Replenisher Storage & Handling Unit

The Chemical Replenishment, storage and handling unit is manufactured of fire retardant polypropylene and is designed, in a specific illustrative embodiment of the invention, to accept five "NOW-PAK" four-liter containers. This unit includes the following:

| |
|---|
| Chemical Replenisher Reservoirs & Level Control (X2) |
| Replenishment Pump Modules |
| Flow Sensors & Multi-Point Headers & Valves |
| Analyzer Sampling Pumps |
| Indicator Lamps |
| Secondary Containment |
| Safety Interlocks |
| Analyzer Waste Collection |
| Audible Alarms |
| Leak Detection |
| Seismic Restraints |

The packaging approach is designed for clean room type environments. A practical embodiment of the present design complies with ST-93, CE "Essential," and UL electrical standards.

In other embodiments, the chemical replenishment, storage and handling unit, manufactured of fire retardant polypropylene, can optionally be designed to accept five "NOW-PAK" 200 liter containers. To accommodate these requirements, the system may include:

a manager/PC controller with G E M/SECS Host communications output;

a automatic chemical analyzer;

a modified, integrated, on-line CVS unit;

a chemical replenisher control unit with custom Now-Pak, 200 liter replenishment system; and a Local Control Unit with tower light, and audible alarm control functions as well as interlock control and monitoring.

In a copper sulfate plating embodiment of the invention, certain problems may arise that need to be addressed and/or repaired. These problems and their respective corrections may be as follows:

| TROUBLE SHOOTING OF ACID COPPER SULFATE PLATING SYSTEM | | |
|---|---|---|
| Problem | Cause | Corrective Action |
| High current density burning | Low Cu, high acid | Analyze and adjust |
| | Low temperature | Heat the bath |
| | Insufficient agitation | Low current, improve agitation |
| | Organic contamination | Carbon Treatment |
| | Low Chloride (bright baths) | Analyze and adjust |
| Loss of brightness | Low additive | Analyze and adjust |
| | Organic Contamination | Analyze, carbon treat |
| | Low chloride | Analyze and adjust |
| | High temperature | Cool the bath |
| | Low Cu | Analyze and adjust |
| Rough deposit | Particles in solution | Filter bath |
| | Torn anode bags | Replace torn bag |
| | Improper anodes | Use phosphorized Cu anodes |
| | Low chloride | Analyze and adjust |

-continued

TROUBLE SHOOTING OF ACID COPPER SULFATE PLATING SYSTEM

| Problem | Cause | Corrective Action |
| --- | --- | --- |
| Pitting | Organic contamination | Analyze, carbon treat |
| | Anode slough | Bag anodes |
| | Low chloride | Analyze and adjust |
| Poor distribution | Low, non-uniform agitation | Improve and adjust |
| | Excessive anode area | Adjust |
| | Improper anode film | Dummy |
| | Current Supply, AC ripple | Adjust to below 10% |
| | Organic contamination | Analyze, carbon treat |
| Low current | Low sulfuric acid | Analyze and adjust |
| | Organic contamination | Analyze, carbon treat |
| | Low additive | Analyze and adjust |
| | High chloride | Analyze and adjust |
| | | Wash anode, dummy plate |
| | | Precipitate and carbon treat |
| | | Dilute |
| | Current density too low | Increase current |
| | High temperature | Cool bath |
| Anode polarization | Tin, Gold contamination | Dummy with Cu foil (no current) |
| | Low temperature | Heat bath |
| | Improper anodes | Bright baths require phosphorized anodes |
| | High chloride | Analyze and adjust |
| | | Wash anode, dummy plate |
| | | Precipitate and carbon treat |
| | | Dilute |
| | High sulfuric acid | Analyze and dilute bath |
| | Low Cu sulfate | Analyze and adjust |
| | Organic contamination | Analyze, carbon treat |

BRIEF DESCRIPTION OF THE DRAWING

Comprehension of the invention is facilitated by reading the following detailed description, in conjunction with the annexed drawing, in which:

FIG. 13 is a representation of a computer screen of the manager system of the present invention, showing a screen representing the replenishment of copper sulfate of a plater;

FIG. 14 is a representation of a computer screen of the manager system of the present invention, showing a feedstock screen;

FIG. 15 is a representation of a computer screen of the manager system of the present invention, showing a copper sulfate settings screen;

DETAILED DESCRIPTION OF AN EMBODIMENT OF THE INVENTION

Figure 1:
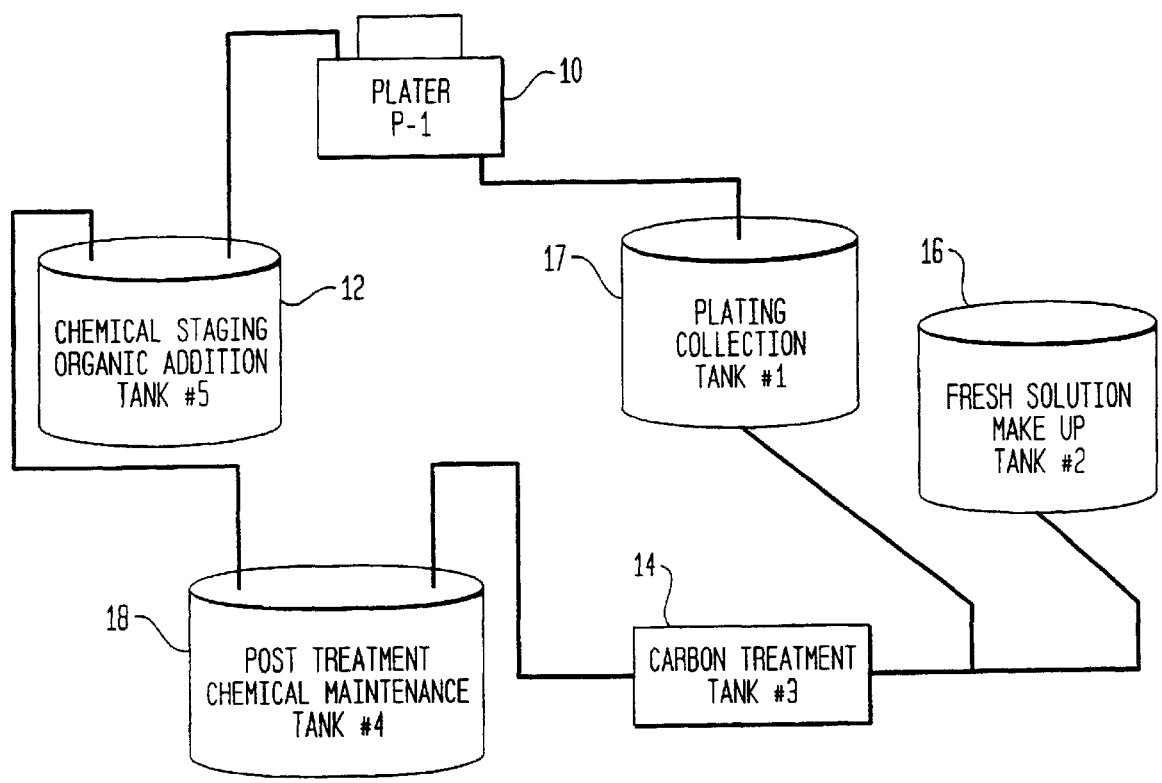
FIG. 1 is a process flow diagram of a specific illustrative embodiment of the invention directed to copper plating operation and chemical control.

FIG. 1 is a process flow diagram of a specific illustrative embodiment of the invention directed to copper plating operation and chemical control. As shown, the system includes a plater 10 that receives material from a chemical staging organic addition tank 12. A carbon treatment tank 14 receives fresh solution from a fresh solution make up tank 16, and collected plating solution from a plating collection tank 17. The carbon treatment tank supplies treated solution to a post treatment chemical maintenance tank 18 that delivers solution to chemical staging organic addition tank 12.

Figure 2:
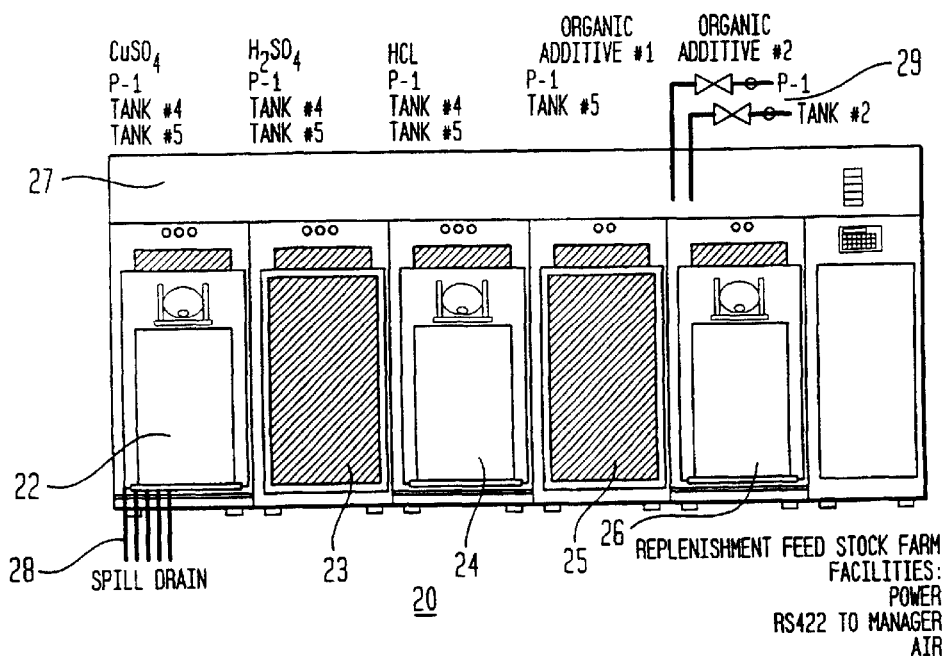
FIG. 2 is a schematic representation of a 200 liter "NOW PAK" automatic dosing system.

FIG. 2 is a schematic representation of a 200 liter "NOW PAK" automatic dosing system 20. In this embodiment, there are provided a $CuSO_4$ tank 22, an $H_2SO_4$ tank 23, an HCl tank 24, and organic additive tanks 25 and 26. The tanks are contained within a housing 27 that is provided with a spill drain 28. A pair of valves 29 for communicating with the tanks is shown schematically.

Figure 3:
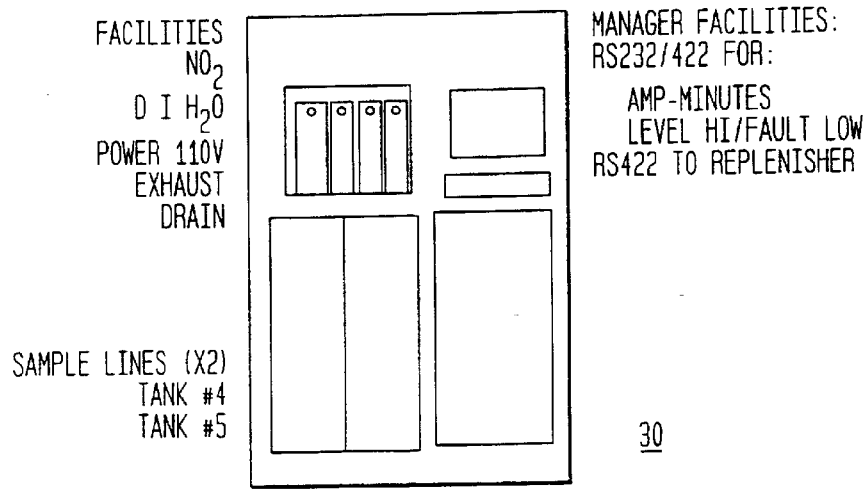
FIG. 3 a simplified plan view of a manager facility the employs RS232/422 data exchange paths in an amp-minute embodiment.

FIG. 3 a simplified plan view of the exterior of a manager facility 30 that employs RS232/422 data exchange paths (not shown) in an amp-minute embodiment.

Figure 4:
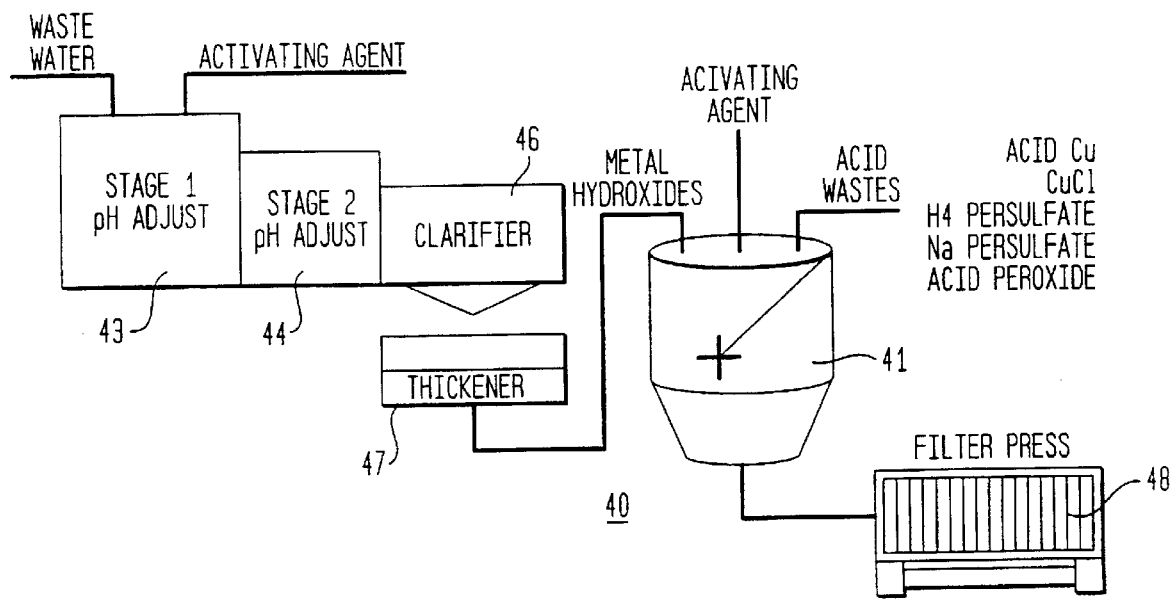
FIG. 4 is a simplified schematic representation of a mixing and filtering arrangement.

FIG. 4 is a simplified schematic representation of a mixing and filtering arrangement 40. Mixing of metal hydroxides, acid wastes, and an activating agent is performed in a mixing tank 41. The acid wastes can include acid Cu, CuCl, H4 persulfate, Na persulfate, and acid peroxide. The metal hydroxides are received at mixing tank 41 from waste water and an activating agent that are combined and subjected to first and second stages of pH adjustment 43 and 44, respectively. The pH adjusted material is then subjected to a clarifier at tank 46 and a thickener 47 is then added. The output of mixing tank 41 is then subjected to a filter press 48.

Figure 5:
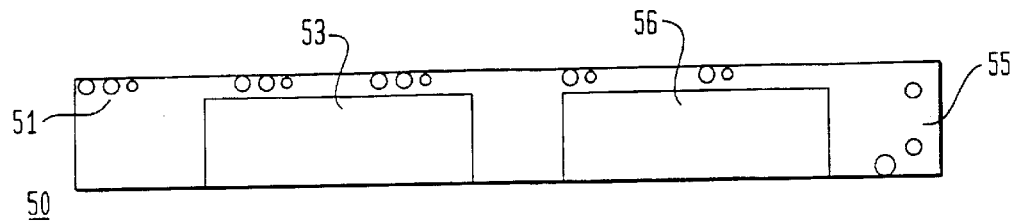
FIG. 5 is a simplified plan view of the exterior of a replenishment system constructed in accordance with the invention.

FIG. 5 is a simplified plan view of the exterior of a replenishment system 50 constructed in accordance with the invention. Replenishment materials are received at replenishment connections 51. Electromechanical devices (not shown in this figure), such as solenoids, pumps, and the like, are contained within a region 53 of the replenishment system, and electrical power and compressed air are received at inlets 55. The power is converted to a low voltage for powering the internal component of the system at a region 56.

Figure 6:
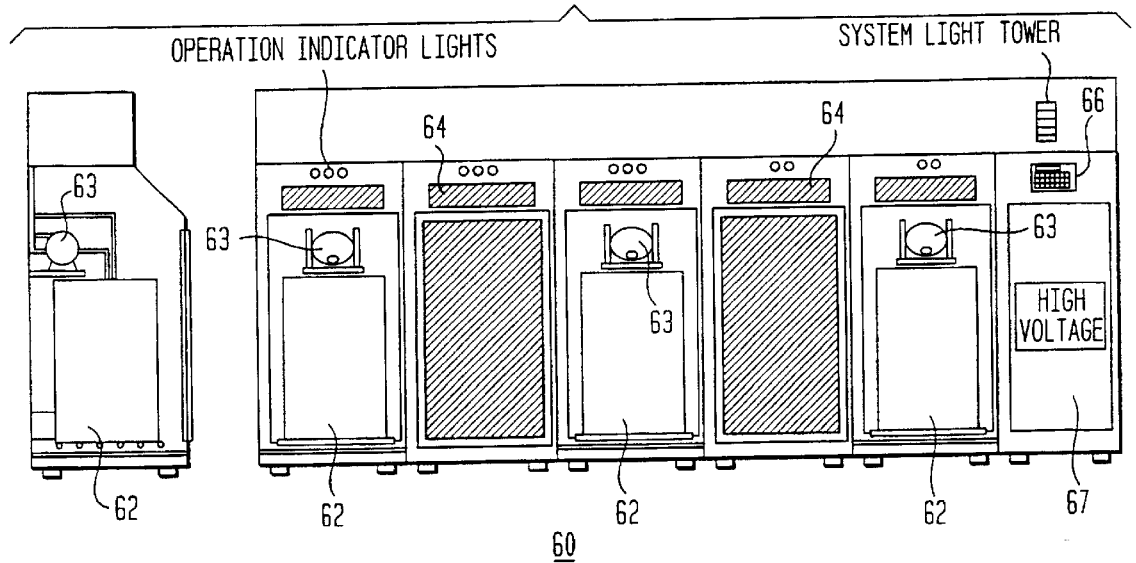
FIG. 6 is a plan representation of a practical embodiment of a 200 liter replenishment system.

FIG. 6 is a plan representation of a practical embodiment of a 200 liter replenishment system 60. In this embodiment, a plurality of 200 liter drums 62 are provided with respectively associated ones of pumps 63. Certain aspects of the process can be viewed at viewing windows 64. Operator control is effected via an operator keypad 66, which in this embodiment of the invention, is installed at high voltage station 67.

Figure 7:
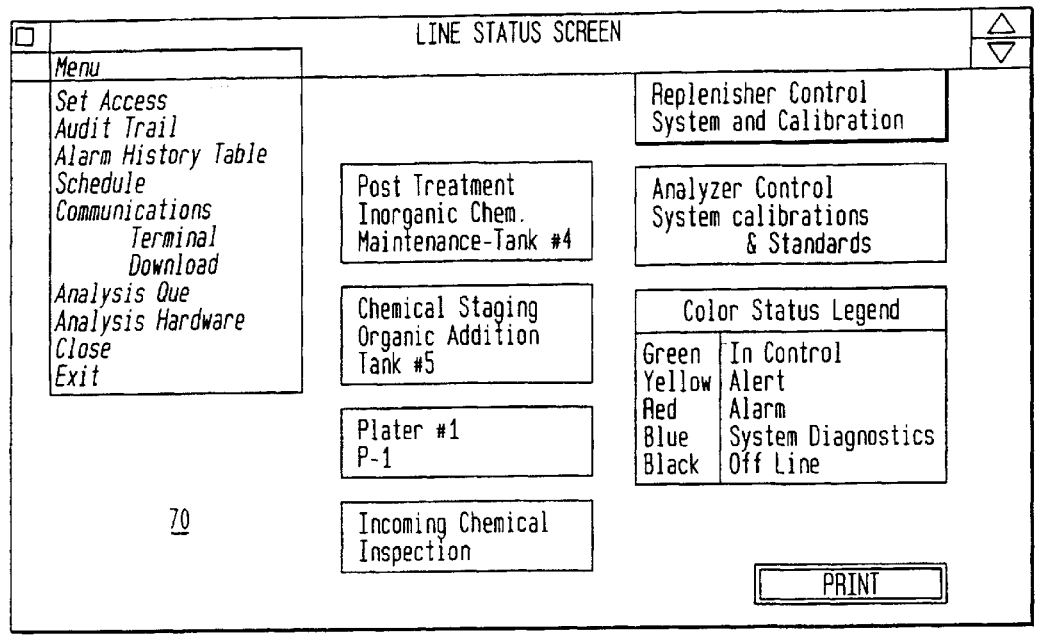
FIG. 7 is a representation of a computer screen of the manager system of the present invention, showing a line status screen.

FIG. 7 is a representation of a main system status computer screen 70 of the manager system of the present invention. The figure shows the various portions of a line status screen.

Figure 8:
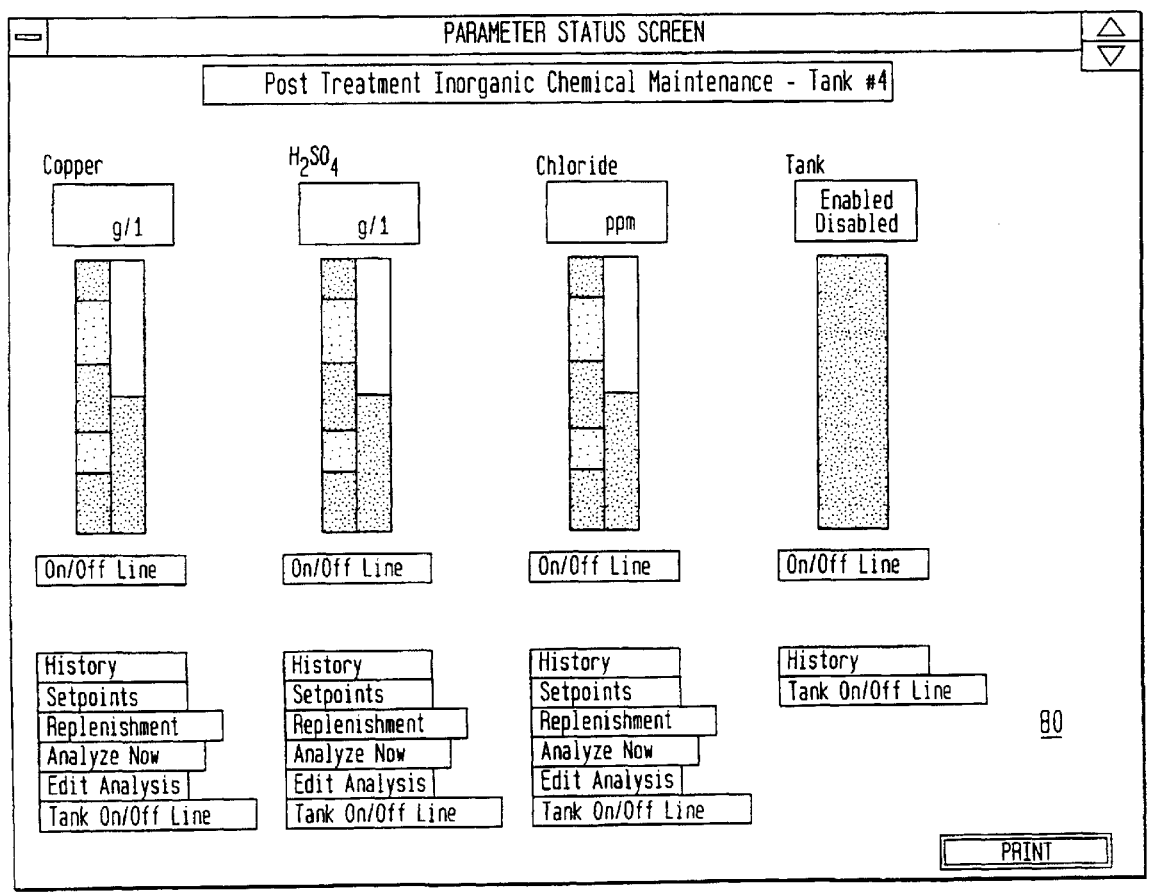
FIG. 8 is a representation of a computer screen of the manager system of the present invention, showing a parameter status screen of post treatment inorganic chemical maintenance.

FIG. 8 is a representation of a computer screen of the manager system of the present invention, showing a parameter status screen 80 of post treatment inorganic chemical maintenance.

Figure 9:
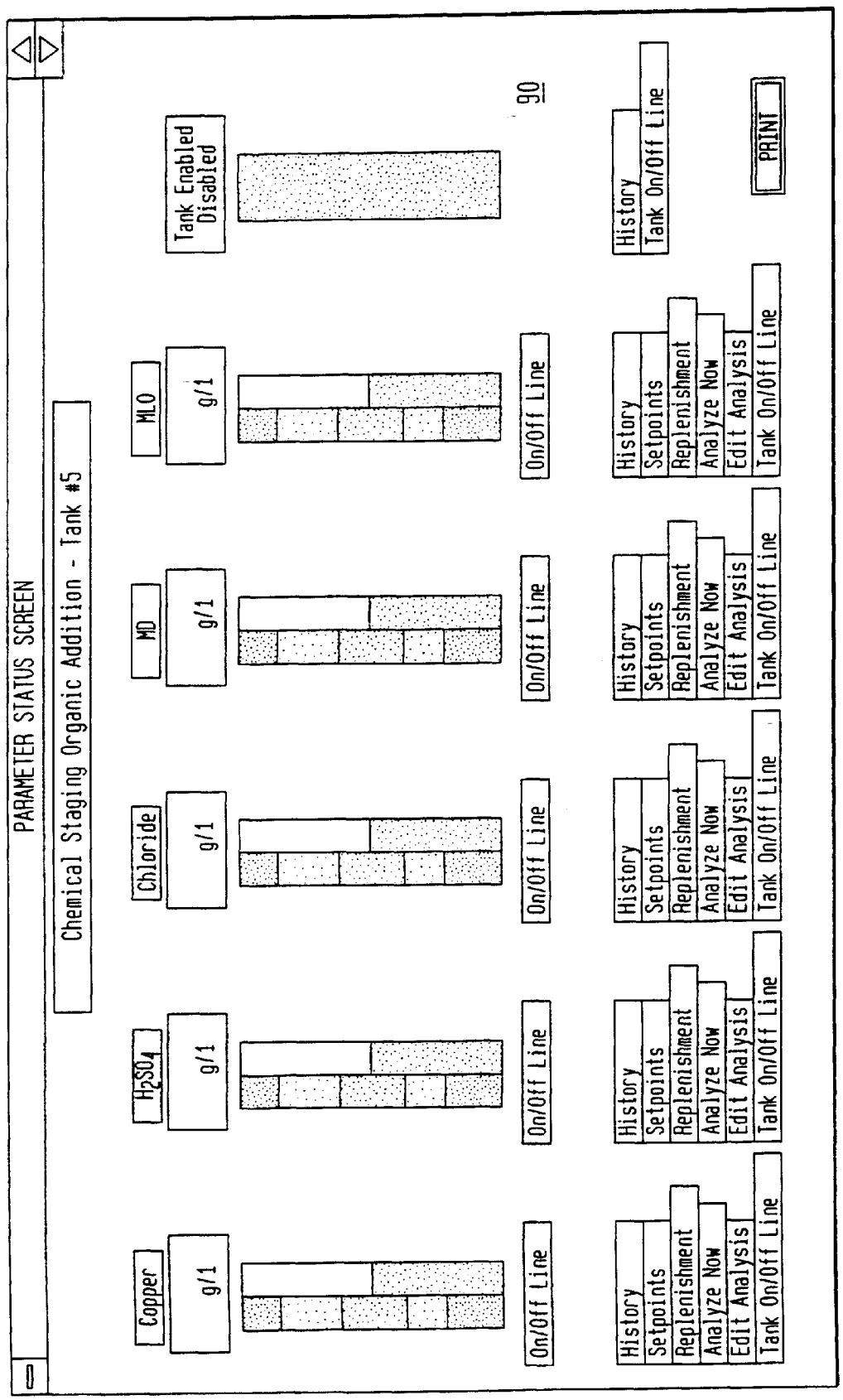
FIG. 9 is a representation of a computer screen of the manager system of the present invention, showing a further parameter status screen of chemical staging organic addition.

FIG. 9 is a representation of a computer screen of the manager system of the present invention, showing a further parameter status screen 90 of chemical staging organic addition.

Figure 10:
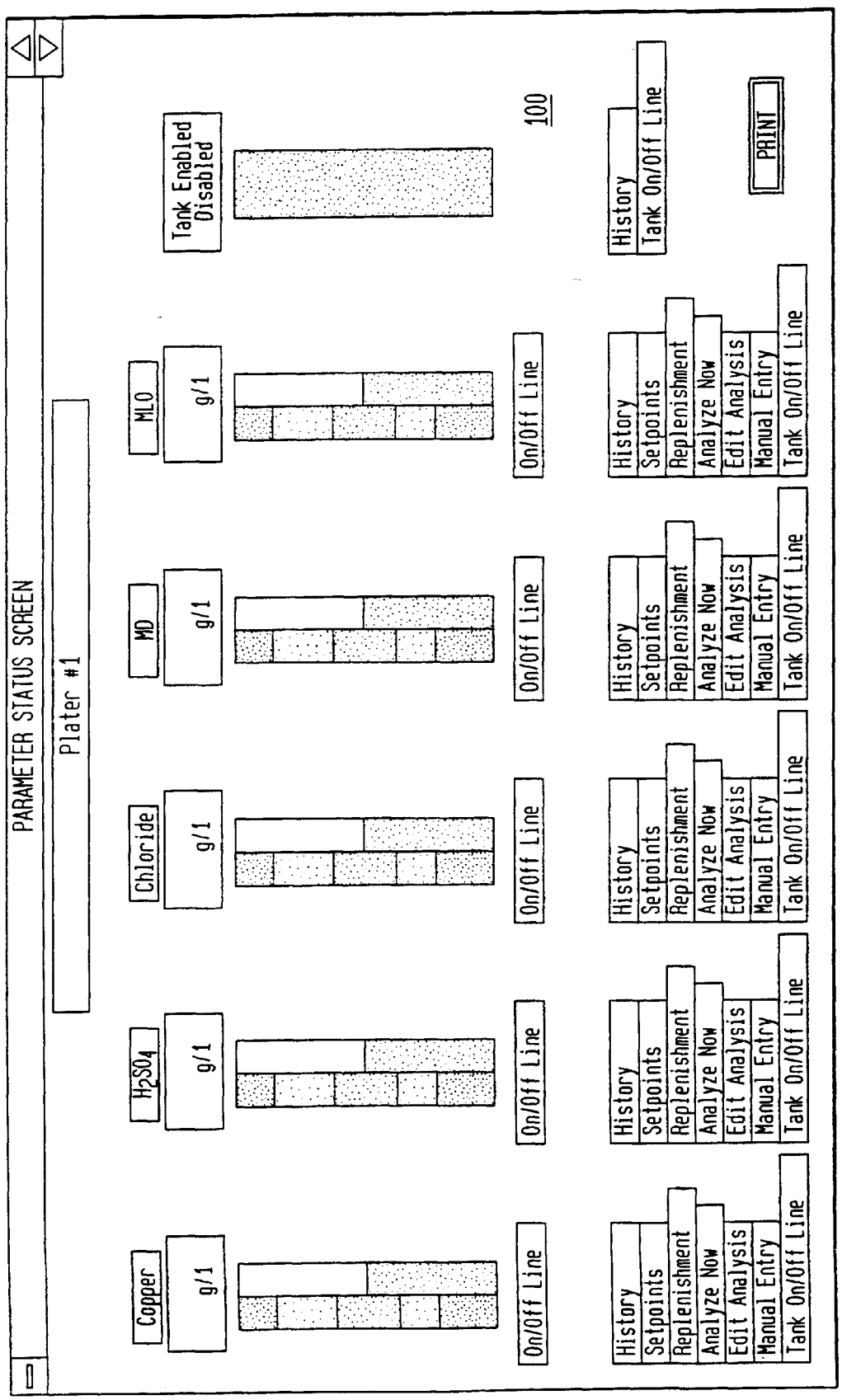
FIG. 10 is a representation of a computer screen of the manager system of the present invention, showing a further parameter status screen of a plater.
Figure 11:
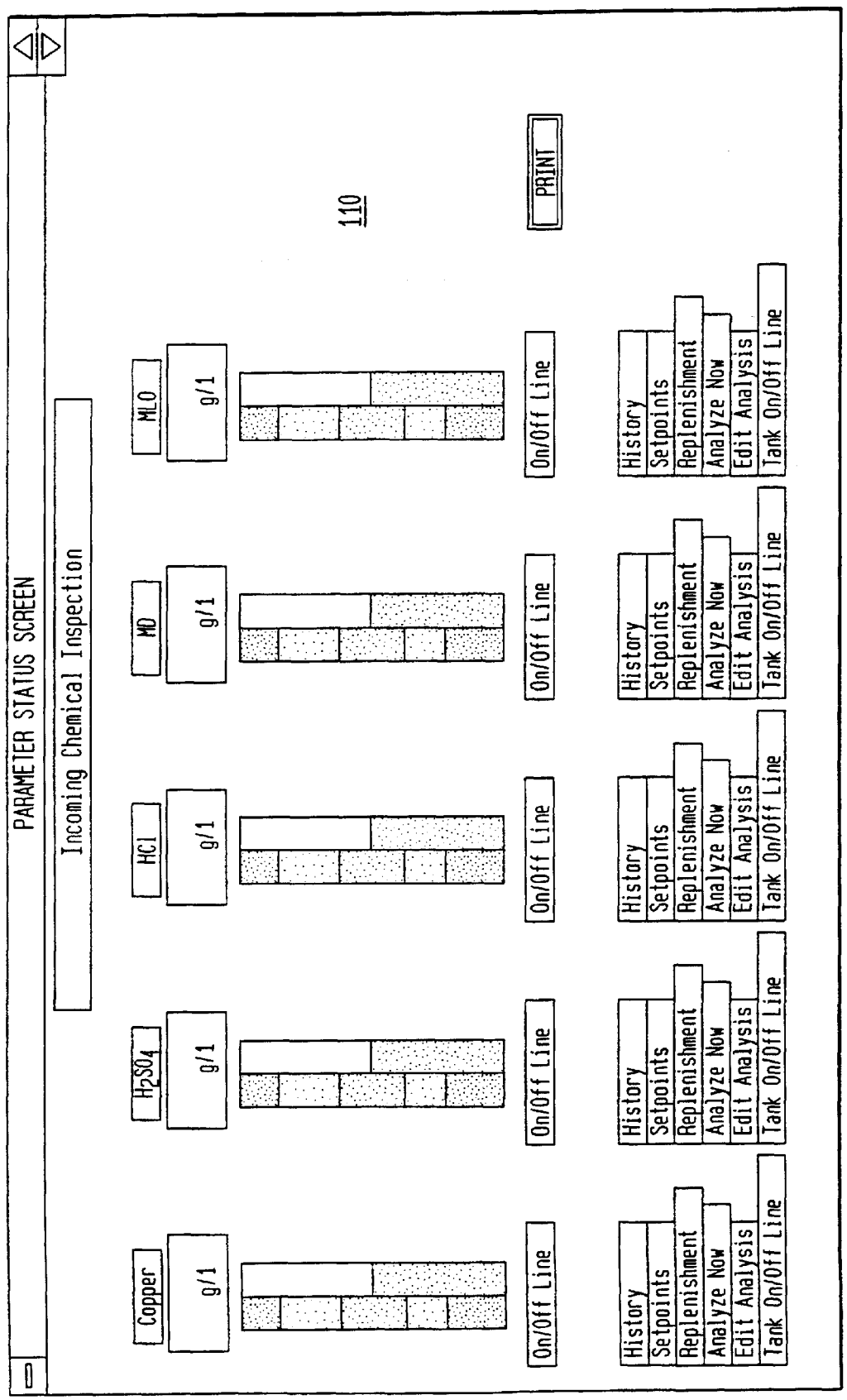
FIG. 11 is a representation of a computer screen of the manager system of the present invention, showing an incoming chemical inspection screen.

FIG. 10 is a representation of a computer screen of the manager system of the present invention, showing a further parameter status screen 100 of a plater;

FIG. 11 is a representation of a computer screen of the manager system of the present invention, showing an incoming chemical inspection screen 110.

Figure 12:
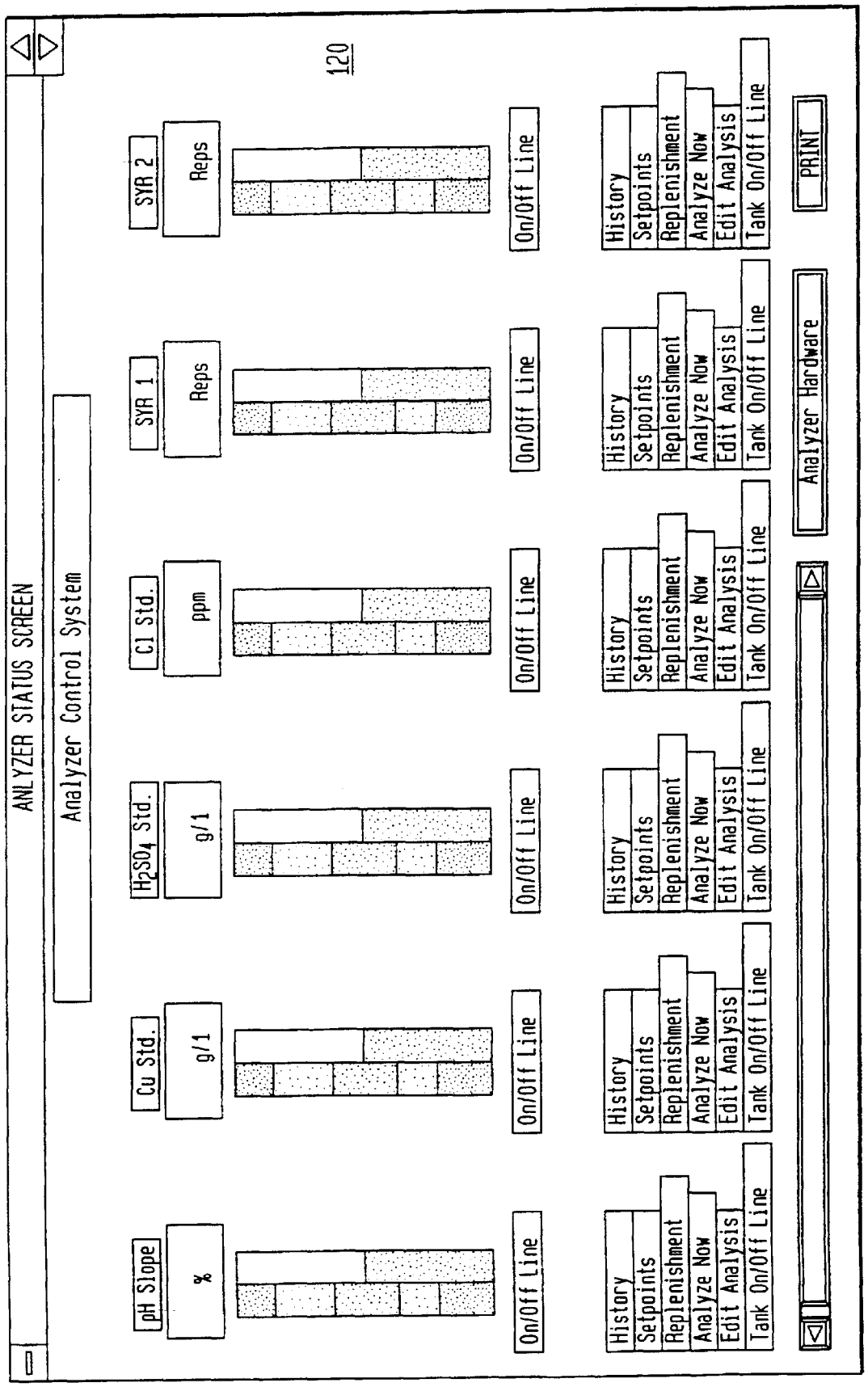
FIG. 12 is a representation of a computer screen of the manager system of the present invention, showing an analyzer control system screen.

FIG. 12 is a representation of a computer screen of the manager system of the present invention, showing an analyzer control system screen 120.

FIG. 13 is a representation of a computer screen of the manager system of the present invention, showing a screen 130 representing the replenishment of copper sulfate of a plater;

FIG. 14 is a representation of a computer screen of the manager system of the present invention, showing a feedstock screen 140.

FIG. 15 is a representation of a computer screen of the manager system of the present invention, showing a copper sulfate settings screen 150.

Figure 16:
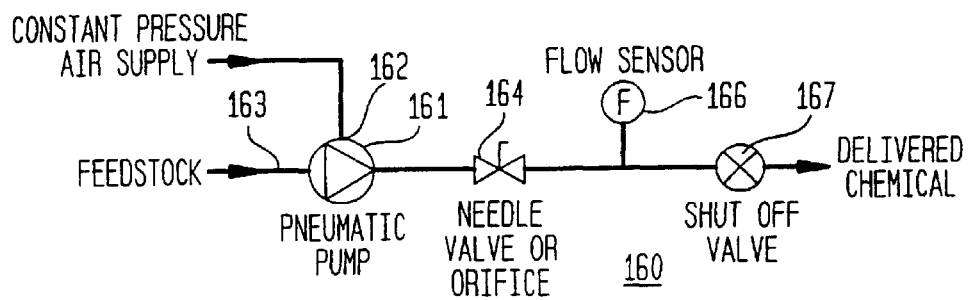
FIG. 16 is a simplified schematic representation of an arrangement that achieves accurate delivery volumes.

FIG. 16 is a simplified schematic representation of an arrangement 160 that achieves accurate delivery volumes. A pneumatic pump 161 receives a supply of air at a constant pressure at an air inlet 162, as well as the feedstock of the chemical desired to be delivered at a feedstock inlet 163. The outlet of pneumatic pump 163 is conducted to a needle valve 164. In some embodiments of the invention, the needle valve may be replaced with an orifice (not shown) of predetermined size. The rate of flow of the chemical at the outlet of the needle valve is monitored by a flow meter 166, and can be controlled by a shut off valve 167. This arrangement produces a highly controlled rate of flow of the chemical to be delivered.

Figure 17:
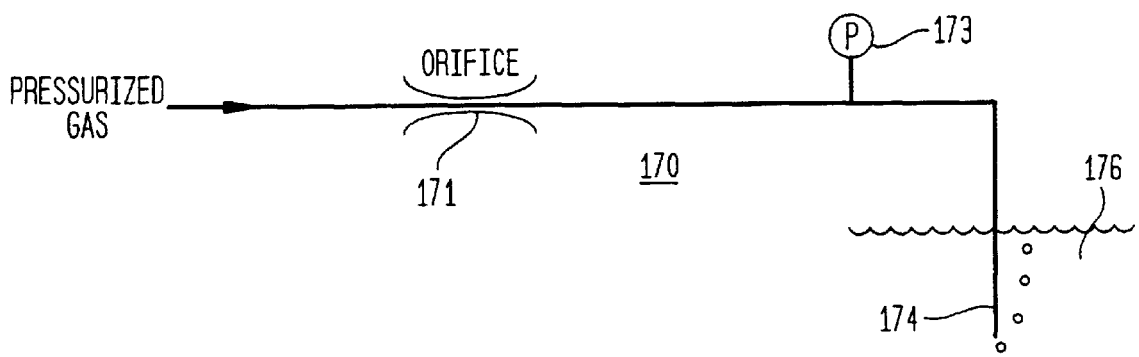
FIG. 17 is a simplified schematic representation of an arrangement that achieves accurate measurement of the level of fluid material in a chemical bath.

FIG. 17 is a simplified schematic representation of an arrangement 170 that achieves accurate measurement of the level of fluid material in a chemical bath. In operation, the pressure of a pressurized gas that has been passed through an orifice 171 is monitored by a pressure gauge 173. The pressurized gas is released at an outlet 174 that is submerged in a chemical bath 176. The pressure reading at pressure gauge 173 constitutes an accurate measure of the level of the chemical bath. There is therefore provided a simple and inexpensive level monitor.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention and should not be construed to limit the scope thereof.

What is claimed is:

1. A method of controlling the content of a chemical bath, the method comprising the steps of:

first determining a rate of continued replenishment of a predetermined constituent of the chemical bath, said step of first determining a rate of continued replenishment, including the further steps of:

establishing a quantum of a replenishment medium; and determining a replenishment frequency corresponding to a rate at which the established quantum of a replenishment medium is deposited in the chemical bath with respect to the replenishment condition;

second determining a replenishment condition for the chemical bath;

defining units of the replenishment condition;

counting elapsed units of the replenishment condition; and adjusting the rate of continued replenishment of the predetermined constituent of the chemical bath in response to the replenishment condition.

2. The method of claim 1, wherein the rate of continued replenishment in said step of first determining is based on an historical replenishment rate.

3. The method of claim 1, wherein said step of second determining a replenishment condition comprises the step of monitoring elapsed time.

4. The method of claim 1, wherein said step of second determining a replenishment condition comprises the step of monitoring the consumption of electrical energy by the chemical bath.

5. The method of claim 1, wherein the chemical bath is a plating bath, and said step of second determining a replenishment condition comprises the step of monitoring the number of products to be plated in the plating bath.

6. The method of claim 1, wherein the chemical bath is a plating bath, and said step of second determining a replenishment condition comprises the step of monitoring the surface area of the products to be plated in the plating bath.

7. The method of claim 1, wherein there is further provided the step of defining a replenishment threshold corresponding to the product of the defined units of the replenishment condition and a predetermined number of units of the replenishment condition.

8. The method of claim 7, wherein said step of adjusting the rate of continued replenishment comprises the step of comparing a counted number of units of the replenishment condition to the predetermined number of units of the replenishment condition.

9. The method of claim 8, wherein said step of adjusting the rate of continued-replenishment comprises the step of determining a rate of adjustment of the rate of continued replenishment.

10. A method of controlling the content of a chemical bath, the method comprising the steps of:

determining a replenishment condition for the chemical bath;

defining a unit of the replenishment condition;

establishing a pacing factor corresponding to a replenishment volume of a replenishment medium per unit of the replenishment condition;

defining a replenishment threshold corresponding to the product of a predetermined number of the defined units of the replenishment condition and the pacing factor;

counting elapsed units of the replenishment condition;

effecting a replenishment of the chemical bath when the replenishment threshold is reached, said step of effecting a replenishment of the chemical bath including the further step of adjusting a determined quantum of the replenishment of the chemical bath in accordance with the relationship:

$$P_F' = P_F \times [1 + (R_A/T) \times A],$$

where, $P_F$=Current pacing factor, in units of replenishment volume per paced unit, $P_F'$=New pacing factor, R=Replenishment amount calculated from current quantitative analysis result, T=Total paced replenishment since last analysis result, and A=Fractional adjustment rate, $0 < A \leq 1$; and testing the chemical bath to determine the content of the chemical bath.

11. The method of claim 10, wherein the step of adjusting the quantum of the replenishment of the chemical bath comprises the further step of varying the replenishment volume of the replenishment medium per unit of the replenishment condition.

12. The method of claim 10, wherein the step of adjusting the replenishment of the chemical bath comprises the further step of varying the replenishment threshold.

13. A method of adjusting the rate of replenishment of a determined component of a chemical composition, the method comprising the steps of:

first taking a prior analytical reading (Previous Reading) of the proportion of the determined component in the chemical composition;

second taking a current analytical reading (Current Reading) of the proportion of the determined component in the chemical composition;

determining a change in accordance with the formula:

Change in Analytical Reading=Current Reading−Previous Reading, and calculating a replenishment error in accordance with the formula:

Paced Replenishment Error=Change in Analytical Reading×Analytical Replenishment Factor−Sum of Non-Paced Replenishments Since Last Analysis.

14. The method of claim 13 wherein there is further provided the step of calculating a new replenishment factor in accordance with the formula:

New Factor=

Old Factor−Old Factor×(Tuning Rate/100)×

Paced Replenishment Error/Sum of Paced Replenishments Since Last Analysis.

* * * * *